United States Patent
Kikuzumi et al.

(10) Patent No.: US 10,302,582 B2
(45) Date of Patent: May 28, 2019

(54) RESISTANCE-MEASUREMENT APPARATUS AND METHOD FOR MEASURING RESISTANCE OF POWDERY MATERIALS

(71) Applicant: Panasonic Intellectual Property Management Co, Ltd., Osaka (JP)

(72) Inventors: Shinya Kikuzumi, Osaka (JP); Shinji Yoshino, Hyogo (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 15/695,004

(22) Filed: Sep. 5, 2017

(65) Prior Publication Data

US 2018/0080892 A1    Mar. 22, 2018

(30) Foreign Application Priority Data

Sep. 21, 2016    (JP) .................................. 2016-183567

(51) Int. Cl.
*G01N 27/04* (2006.01)
*G01N 33/20* (2019.01)
*G01N 33/00* (2006.01)

(52) U.S. Cl.
CPC ........... *G01N 27/043* (2013.01); *G01N 33/20* (2013.01); *G01N 2033/0091* (2013.01)

(58) Field of Classification Search
CPC .................................................. G01N 27/043
See application file for complete search history.

(56) References Cited

U.S. PATENT DOCUMENTS

| | | | | | |
|---|---|---|---|---|---|
| 4,975,412 | A | * | 12/1990 | Okazaki ................ | C04B 35/645 264/451 |
| 5,451,882 | A | * | 9/1995 | Wakino .............. | G01R 27/2688 324/663 |
| 6,030,507 | A | * | 2/2000 | Lupton ................. | C01B 13/322 204/164 |
| 2014/0285221 | A1 | * | 9/2014 | Fijalkowski ......... | G01N 27/026 324/663 |

FOREIGN PATENT DOCUMENTS

| | | | |
|---|---|---|---|
| CN | 203164294 U | * | 8/2013 |
| JP | 02226043 A | * | 9/1990 |
| JP | 2016-027316 | | 2/2016 |

* cited by examiner

*Primary Examiner* — Walter L Lindsay, Jr.
*Assistant Examiner* — Milton Gonzalez
(74) *Attorney, Agent, or Firm* — Wenderoth, Lind & Ponack, L.L.P.

(57) ABSTRACT

Disclosed is a resistance-measurement apparatus, including: multiple measurement chambers for holding powdery materials; multiple first electrodes that press the respective powder materials in the measurement chambers; at least one second electrode that faces the first electrodes and that presses the powdery materials; and a measuring device that measures a resistance between the first electrodes and the at least one second electrode. Further disclosed is a resistance-measurement method, including: (i) placing at least one powdery material between a number N of first electrodes and at least one second electrode, and pressing the at least one powdery material therebetween; (ii) measuring an impedance between the number N of the first electrodes and the at least one second electrode; and (iii) measuring an impedance between a number M of the first electrodes and the at least one second electrode, wherein the number N is different from the number M.

14 Claims, 8 Drawing Sheets

RESISTANCE-MEASUREMENT APPARATUS AND METHOD FOR MEASURING RESISTANCE OF POWDERY MATERIALS

TECHNICAL FIELD

The technical field relates to resistance-measurement apparatuses and methods. In particular, the technical field relates to resistance-measurement apparatuses and methods that are employed for evaluations of powdery materials.

BACKGROUND

In recent years, the importance of selection and rapid development of materials has increased, for the purposes of improving performance of products and speeding up their development time.

Taking polymer electrolyte fuel cells (PEFCs) as an example, catalyst layers and gas-diffusion layers are joined in sequence onto both outer surfaces of electrolyte membranes in which power-generation reactions occur, thereby forming membrane/electrode assemblies. Then, the membrane/electrode assemblies are each placed between separators to produce single cells, and a required number of the multiple single cells are stacked to produce polymer electrolyte fuel cells.

A fuel gas containing hydrogen, and an oxidant gas containing oxygen (e.g., the air) are supplied to such polymer electrolyte fuel cells, and thus, the fuel gas and the oxidant gas are electrochemically reacted with each other through the electrolyte membranes. As a result, the polymer electrolyte fuel cells simultaneously produce electric power, heat and water.

A reaction represented by Formula 1 and a reaction represented by Formula 2 occur in negative electrodes and positive electrodes, respectively.

$$H_2 \rightarrow 2H^+ + 2e^- \quad \text{(Formula 1)}$$

$$\tfrac{1}{2} O_2 + 2H^+ + 2e^- \rightarrow H_2O \quad \text{(Formula 2)}$$

Hydrogen ions ($H^+$; protons) produced through the reaction in the negative electrodes move inside the electrolyte membranes, and are consumed in the reaction in the positive electrodes. Such electrode reactions occur in the catalyst layers. The catalyst layers are configured by catalyst-supported carbon materials and electrolytes, and thus, the electrode reactions proceed in boundary faces between the catalysts supported onto the carbon materials and the electrolytes. Furthermore, connections between the carbon materials within the catalyst layers serve as pathways for electrons, and connections between the electrolytes serve as pathways for hydrogen ions. In addition, platinum would often be employed for the catalysts supported for both, the positive and negative electrodes. Platinum-based alloy catalysts may also be employed to improve the activities of the positive electrodes and the resistance of the negative electrodes to CO.

Thus, the performance of the catalysts is directly linked to performance of fuel cells. Furthermore, metal materials used for the catalysts (e.g., platinum) are very expensive, and therefore, it would be important to determine their performance at an early stage of the development and by use of smaller amounts.

In view of the above-mentioned issues, measurements of physical properties of the materials are very important, and it is desired that the measurements are carried out by using catalyst powder forms of the materials, i.e., in states that are similar to forms of the materials to be used.

With regards to a method for measuring a resistance of a powdery material, a method in which DC voltages are applied to powdery materials, electric currents generated in that case are measured, and then, resistance values are obtained based on Ohm's law has generally been employed. However, an AC impedance method has been proposed as a more-highly-accurate measurement method (JP-A-2016-27316).

In the AC impedance method disclosed in JP-A-2016-27316, a pair of electrodes are placed at the upper and lower side of a powdery material that is a test subject, and then, an AC voltage or current is applied (input) to the electrodes while varying the frequency. Impedances are calculated based on output currents or voltages corresponding to the input AC voltages or currents. Relationships between frequencies of the input signals and the impedances are computed, the Nyquist plot is conducted, and a shape of the Nyquist plot is subjected to equivalent circuit fitting. According to these procedures, it becomes possible to measure resistance components accurately.

FIG. 8 is a schematic view that describes the conventional method for measuring a resistance of a powdery material. Arrangements among the components required in the powder resistance-measurement method in FIG. 8 will described below.

A measurement vessel 51 is configured by side-wall sections 52, a bottom 57, and a cover 58. The bottom 57 is configured by a bottom insulation part 57a, a bottom electrode 57b, and a bottom terminal 54. The cover 58 is configured by a cover insulation part 58a, a cover electrode 58b, and a cover terminal 53.

A powdery material 59 that is a measurement sample is put into an internal space 56, and is placed between the bottom electrode 57b and the cover electrode 58b. In a state in which a pressing device 60 applies pressure to the measurement sample 59, impedances are measured between the cover terminal 53 and the bottom terminal 54.

SUMMARY

However, since diameters of the electrodes in the method disclosed in the JP-A-2016-273616 are from 1 to 3 cm, large amounts of samples would be required for the measurements.

In consideration of the above-mentioned problem, an objective of the disclosure is to provide a resistance-measurement apparatus and method that make it possible to achieve a measurement even when only minute amounts of powdery measurement samples are available.

In order to achieve the above objective, according to an aspect of the disclosure, provided is a resistance-measurement apparatus, including: multiple measurement chambers for holding powdery materials; multiple first electrodes that press the respective powder materials in the measurement chambers; at least one second electrode that faces the first electrodes and that presses the powdery materials; and a measuring device that measures a resistance between the first electrodes and the at least one second electrode.

Furthermore, according to another aspect of the disclosure, provided is a resistance-measurement method, including: (i) placing at least one powdery material between a number N of first electrodes and at least one second electrode, and pressing the at least one powdery material therebetween; iii) measuring an impedance between the number N of the first electrodes and the at least one second electrode; and (iii) measuring an impedance between a number M of the first electrodes and the at least one second electrode, wherein the number N is different from the number M.

According to the disclosure, resistance-measurement apparatuses and methods can easily carry out the measurement even when only minute amounts of powdery measurement samples are available.

DESCRIPTION OF EMBODIMENTS

Hereinafter, embodiments of the disclosure will be described with reference to FIGS. 1 to 5.
<Structure of Apparatus>

Figure 1:
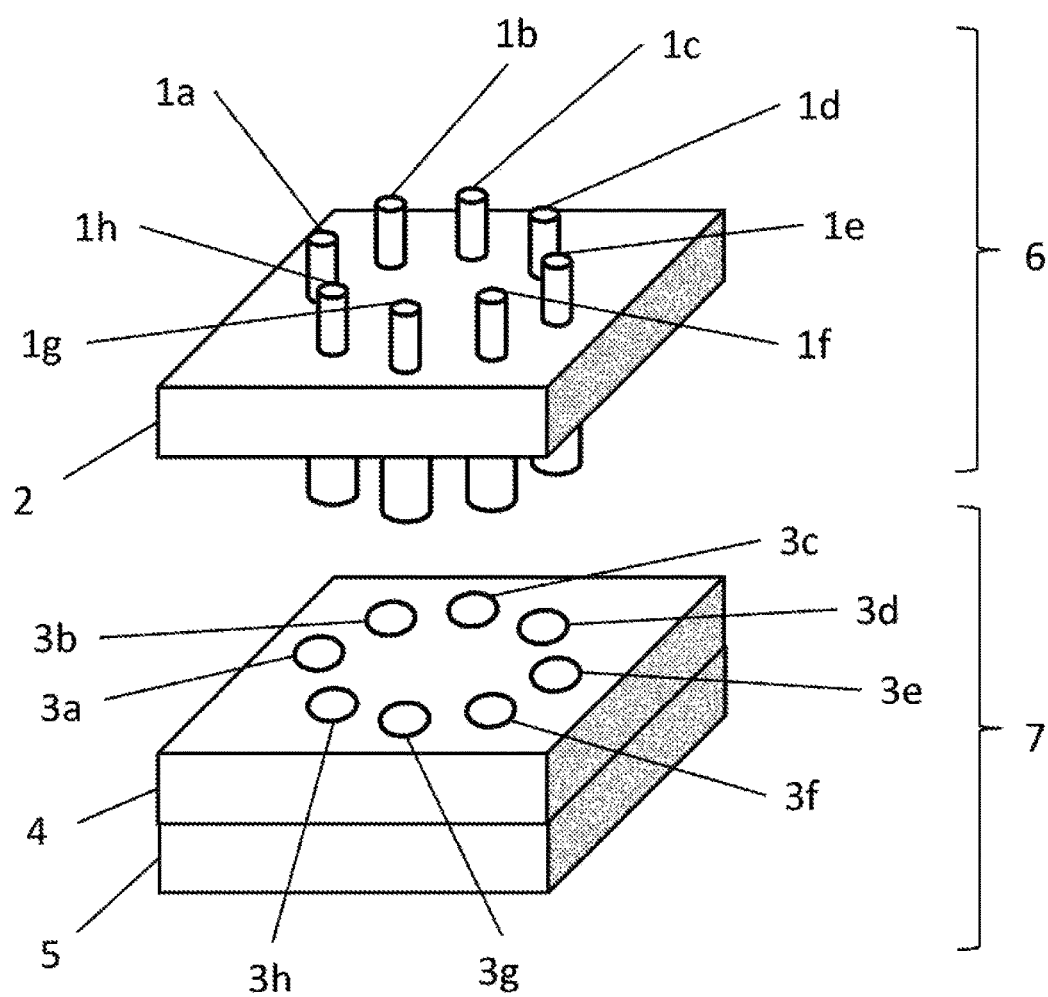
FIG. 1 is a schematic view of measurement of resistance of powdery materials in an embodiment.

FIG. 1 is a schematic view of a measurement unit 8 in a resistance-measurement apparatus according to an embodiment. The measurement unit 8 includes a first electrode unit 6 and a second electrode unit 7.

The first electrode unit 6 is provided with a first electrodes 1a to 1h, and a first insulator 2. The first electrodes 1a to 1h are each formed of an electrically-conductive material. The first insulator 2 is formed of an electrically-insulative material. The first electrodes 1a to 1h are immobilized to the first insulator 2 in such a manner that they are electrically insulated from each other. The first electrodes 1a to 1h are each rod-shaped, and penetrate through the planar first insulator 2, and appears on the both sides of the first insulator 2.

The second electrode unit 7 is provided with a second insulator 4 and a second electrode 5. The second insulator 4 and the second electrode 5 are formed in a flat plate shape, and are stacked. The second insulator 4 is located adjacently to the first electrode unit 6. The second insulator 4 is formed of an electrically-insulative material, and is provided with measurement chambers 3a to 3h (a measurement chamber 3).

The second insulator 4 and the second electrode 5 are fixed to one another in a state in which bottoms of the measurement chambers 3a to 3h are configured by the second electrode 5.

The second electrode 5 is formed of a porous material (e.g., a sintered metal material) that is electrically conductive. The second electrode 5 is configured in such a manner that a gas supplied through a lateral or bottom surface of the second electrode 5 is supplied to the measurement chambers 3a to 3h (not shown in the figures).

Figure 2A:
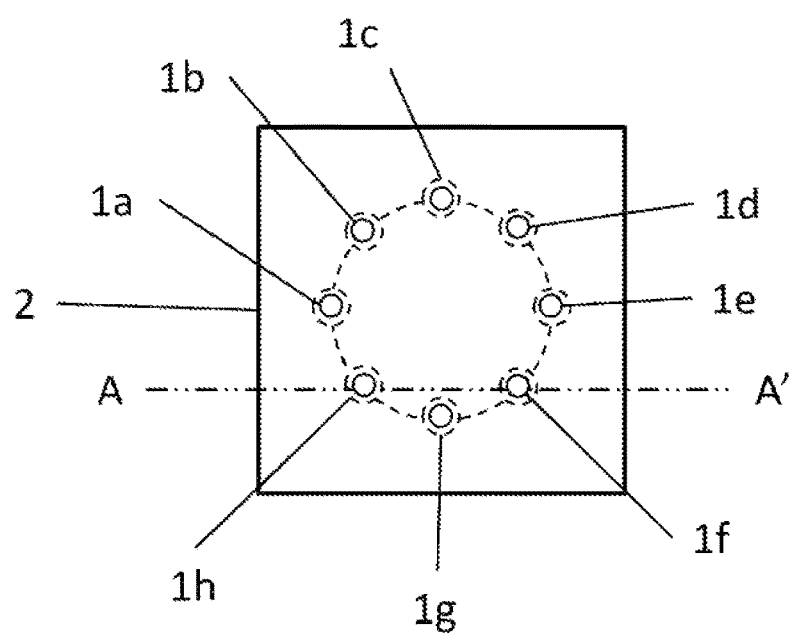
FIG. 2A is a top plan view of a first electrode unit in an embodiment.
Figure 2B:
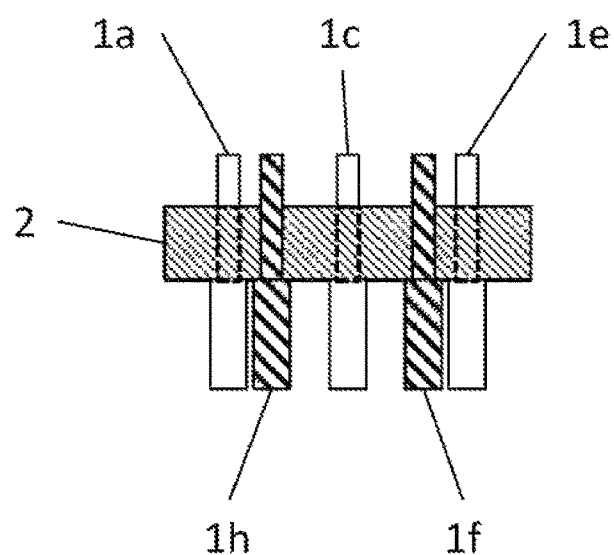
FIG. 2B is a cross-section view of a first electrode unit in an embodiment.

FIG. 2A is a top plan view of the first electrode unit 6. FIG. 2B is a cross-section view of the first electrode unit 6. The first electrodes 1a to 1h and the first insulator 2 are immobilized to one another in a state in which they are electrically insulated. In FIGS. 2A and 2B, conveniently, eight first electrodes 1a to 1h are arranged in a concentric pattern. However, the number of first electrodes, and arrangement patterns therefor are not limited to such an embodiment. As described below, the first electrodes 1a to 1h and the second electrode 5 are pressed against one another. In this case, they are preferably arranged in such a manner that the pressure is evenly applied to the first electrodes 1a to 1h. It is preferable that the first electrodes 1a to 1h are arranged in a concentric or symmetric pattern.

Figure 3A:
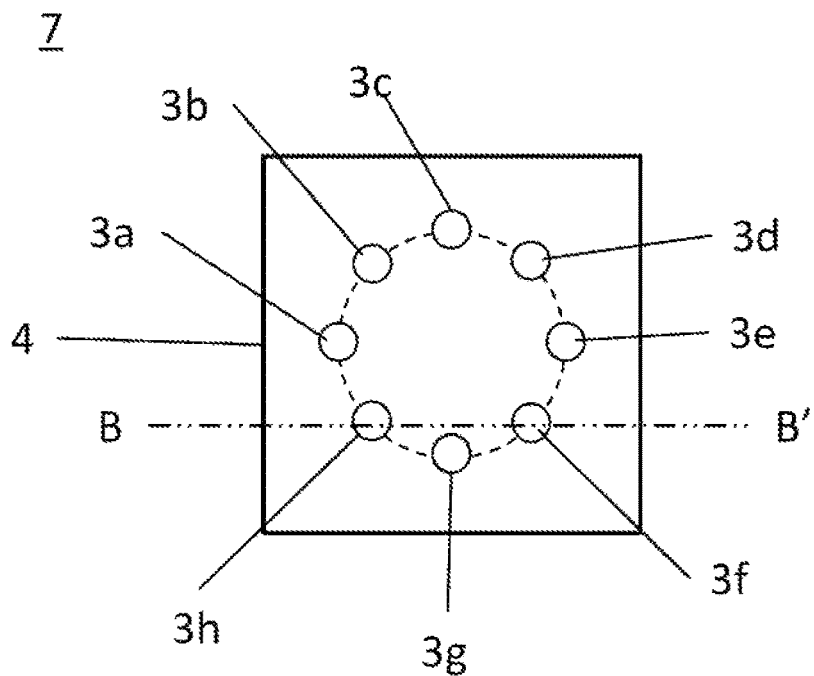
FIG. 3A is a top plan view of a second electrode unit in an embodiment.
Figure 3B:
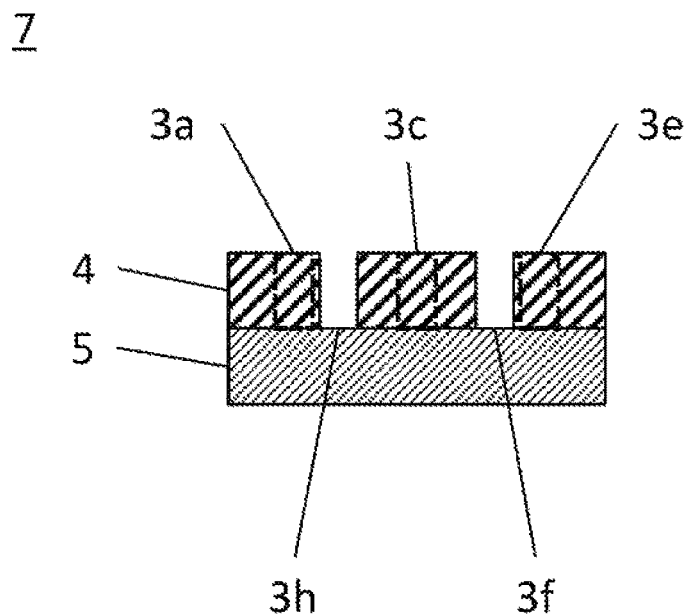
FIG. 3B is a cross-section view of a second electrode unit in an embodiment.

FIG. 3A is a top plan view of the second electrode unit 7. FIG. 3B is a cross-section view of the second electrode unit 7. The measurement chambers 3a to 3h are configured by forming through-holes in the second insulator 4. The second insulator 4 and the second electrode 5 are immobilized to one another in a state in which the bottoms of the measurement chambers 3a to 3h are formed by the second electrode 5. The measurement chambers 3a to 3h are paired with or provided facing the first electrode 1, on a one-to-one basis. The first electrodes 1a to 1h are inserted into the measurement chambers 3a to 3h.

Although, in FIGS. 3A and 3B, eight measurement chambers 3a to 3h are conveniently arranged in a concentric pattern, the number of measurement chambers and arrangement patterns therefor are not limited to such a configuration. However, it would be required that the location of the first electrodes 1 and the locations of the measurement chambers 3 agree with (or are arranged somehow correspondingly to) each other. That is, the first electrodes 1 and the measurement chambers 3 may be paired with each other.
<Sets of Measurement Objects>

Figure 4A:
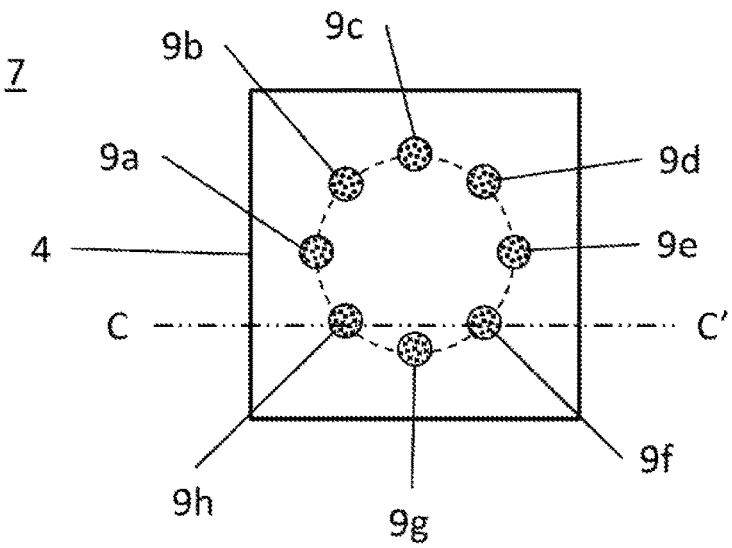
FIG. 4A is a plan view that shows relative positions between test samples and electrodes in an embodiment.
Figure 4B:
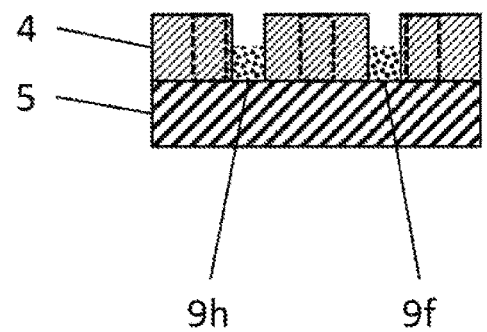
FIG. 4B is a cross-section view that shows relative positions between test samples and electrodes in an embodiment.
Figure 4C:
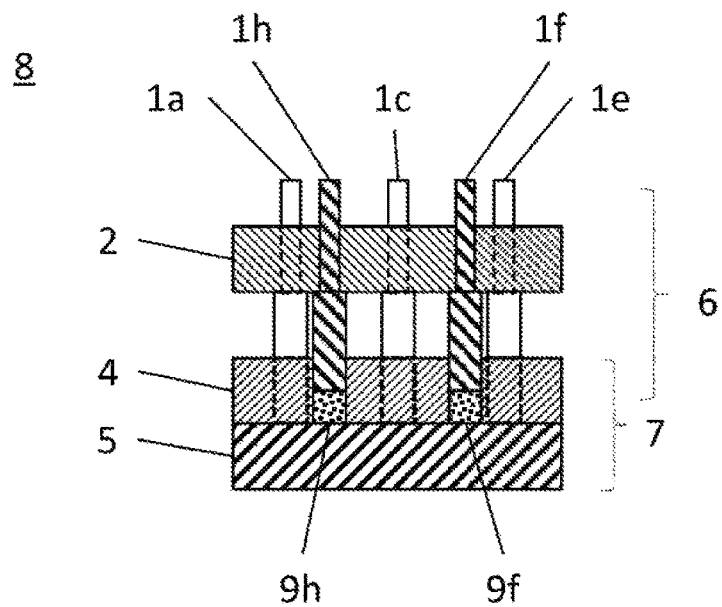
FIG. 4C is a cross-section view that shows relative positions between test samples and a measurement unit in as embodiment.

In FIGS. 4A and 4B, relative positions between test samples 9a to 9h (test sample 9; test objects) and the second electrode unit 7 are shown. FIG. 4A is a top plan view of the second electrode unit 7 in which the test samples 9a to 9h are placed. FIG. 4B is a cross-section view of the second electrode unit 7 in which the test samples 9a to 9h are placed. FIG. 4C is cross-section view of the measurement unit 1 when the measurement is conducted to the test samples 9a to 9h.

The same amounts of the test samples 9a to 9h are placed in the respective measurement chambers 3a to 3h. The test samples 9a to 9h are brought into contact with the second electrode 5 at bottoms of the measurement chambers 3a to 3h. The first electrodes 1a to 1h are located so as to be in contact with top parts of the test samples 9a to 9h. The test samples 9a to 9h are held in spaces formed by the respective first electrodes 1a to 1h, the respective measurement chambers 3a to 3h, and the second electrode 5.

An area of each of the measurement chambers 3a to 3h is preferably from 1 mm$^2$ to 20 mm$^2$, and a depth of each of the measurement chambers 3a to 3h is preferably from 1 mm to 10 mm. In this case, supposing that the measurement chambers 3a to 3h are formed in cylindrical shapes, the area refers to an area of a circle of the cross-section of each of the cylindrical shapes. Supposing that the measurement chambers 3a to 3h are formed in cylindrical shapes, the depth refers to a height of each of the cylindrical shapes.

If the area is smaller than 1 mm², it may be difficult to put the test samples 9a to 9h into the respective measurement chambers 3a to 3h, and therefore, it may be impossible to accurately carry out the measurement.

If the area is larger than 20 mm², amounts of test samples 9a to 9h put into the respective measurement chambers 3a to 3h may be increased.

If the depth is smaller than 1 mm, it may become difficult to hold the test samples 9a to 9h, and therefore, it may be impossible to carry out accurate measurements.

If the depth is larger than 10 mm, amounts of test samples 9a to 9h put into the measurement chambers 3a to 3h may be increased.

In addition, although only one second electrode 5 is preferably provided, the second electrodes 5 may be configured by multiple members. It would be acceptable that multiple members communicate with each other so as to serve as one second electrode 5. Alternatively, multiple second electrodes 5 may be provided correspondingly to the first electrodes 1 and the measurement chambers 3.

<Overall Structure of the Apparatus>

Figure 5:
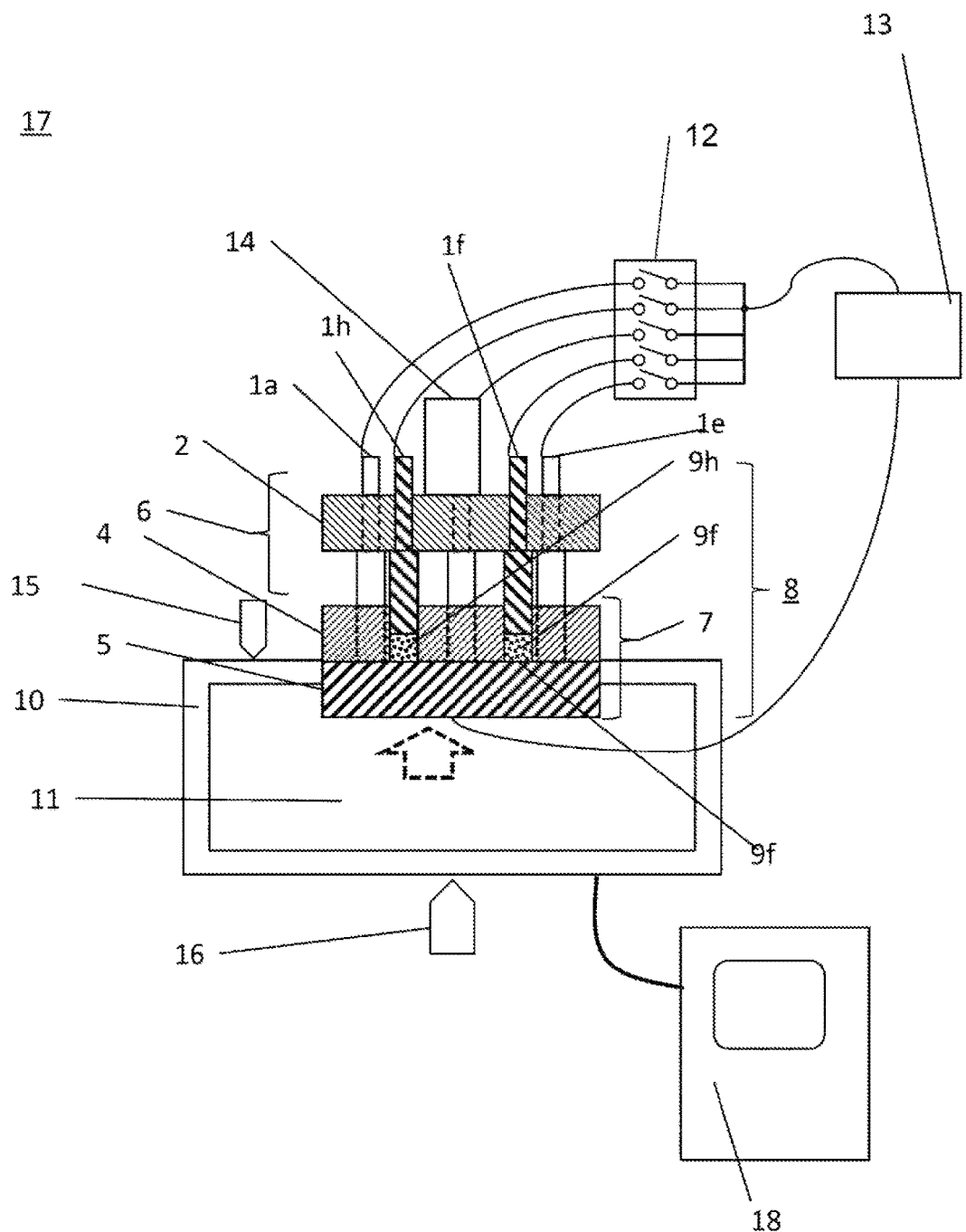
FIG. 5 is a schematic view of an apparatus for measurement of resistance of powdery materials in an embodiment.

FIG. 5 is a schematic view of a resistance-measurement apparatus 17 according to the present embodiment. Positional relationships among elements in the resistance-measurement apparatus 17 in FIG. 5 will be described below.

<Preparation>

At first, the test samples 9a to 9h are put into the measurement chambers 3a to 3h, and the measurement unit 8 is assembled. That is, starting from the state shown in FIG. 4B, the first electrodes 1a to 1h are inserted into the respective measurement chambers 3a to 3h so as to press the test samples 9a to 9h, as shown in FIG. 4C.

Then, the measurement unit 8 is placed onto a gas vessel 10. The second electrode 5 is placed so as to be exposed to a gas-flow channel 11 inside the gas vessel 10. The gas vessel 10 has a role in supplying a gas supplied from the gas-flow channel 11 to the measurement chambers 3a to 3h through the second electrode 5. In this case, the second electrode 5 has gas permeability.

In addition, it would be sufficient that at least one member selected from the group consisting of the first electrodes 1, the second electrode(s) 5, and the measurement chambers 3 has gas permeability, and is connected to the gas-flow channel 11.

Then, the measurement unit 8 and the gas vessel 10 are installed in the resistance-measurement apparatus 17 that is provided with a signal selector 12, a measuring device 13, a pressure-sensitive element 14, and a thickness-measuring device 15. The measuring device 13 is an impedance meter.

The pressure-sensitive element 14 has a role in causing the second electrode unit 7 to actuate through the pressing unit 16, and measuring pressures caused when the first electrodes 1a to 1h are brought into contact with the respective test samples 9a to 9h.

The thickness-measuring device 15 has a role in measuring the level of the top surface of the gas vessel 10. That is, the thickness of the test samples 9a to 9h is measured by the thickness-measuring device 15.

Finally, the first electrode unit 6 and the pressure-sensitive element 14 are connected with each other. The first electrodes 1a to 1h are connected to the signal selector 12. The signal selector 12 has a role in selecting, from among the multiple first electrodes, an electrode to be employed for the measurement. That is, the signal selector 12 selects electrical connections between the multiple first electrodes 1a to 1h and the measuring device 13. The measuring device 13 connects the signal selector 12 and the second electrode 5, and measures an impedance between the first electrode(s) 1 and the second electrode 5.

<Measurement>

(i) First Pressing Step

By use of a pressing unit 16, the second electrode unit 7 is actuated to bring the first electrodes 1a to 1h into contact with the test samples 9a to 9h, thereby applying a predetermined pressure thereto. Additionally, the level of the top surface of the gas vessel 10 at that time is measured by the thickness-measuring device 15, and thus, a difference between the measured level and a level of the top surface of the gas vessel 10 measured when any test samples 9a to 9h are not disposed therein is considered as a thickness of the test samples 9a to 9h.

To simplify descriptions, the gas is supplied from the second electrode 5 to the measurement chambers 3a to 3h in this embodiment. However, the second insulator 4, which forms the measurement chambers 3a to 3h, may be formed of a porous material, and thus, the gas may be supplied from the lateral surfaces of the measurement chambers 3a to 3h to the measurement chambers 3a to 3h. In the same manner, the gas may be supplied from the first electrodes 1a to 1h. Additionally, with regard to the pressing direction, a configuration in which the first electrode unit 6 is immobilized, and the second electrode unit 7 is caused to move is adopted in this embodiment. However, alternatively, a configuration in which the second electrode unit 7 is immobilized, and the first electrode unit 6 is caused to move may be adopted.

(ii) First Measurement Step

To measure resistivities of the test samples 9a to 9h in the above-described arrangement, voltages in the thickness direction of the test samples 9a to 9h are measured in a state in which AC currents are applied thereto. Alternatively, currents passing through the test samples 9a to 9h are measured in a state in which AC voltages are applied thereto.

In this measurement, the measuring device 13 is used to measure a value of the impedance. Supposing that R is a value of impedance obtained as a measurement result, L is a thickness of the powdery catalyst (i.e., a distance between the electrodes), and S is an area of one of the first electrodes, a resistivity of the powdery catalyst can be obtained based on the following formula (3).

$$\text{Resistivity } (\Omega \cdot cm) = R \cdot S/L \quad (3)$$

(iii) Second Measurement Step

By using a number of first electrodes different from the number of the first electrodes 1 used in the first measurement step, the second measurement step is carried out. A number N of the first electrodes 1 are used in the first measurement step, and a number M (different from N) of the first electrodes are used to carry out the second measurement step.

In the measurement method according to this embodiment, by connecting an electric wire coming out of each of the first electrodes 1 to the signal selector 12, the measurement is conducted by way of individually using the first electrodes 1a to 1h, or combining the first electrodes 1a to 1h.

Specifically, in cases where two first electrodes are connected in parallel, the area would be doubled. In cases where three first electrodes are connected in parallel, the area would be tripled. In cases where four first electrodes are connected in parallel, the area would be quadrupled.

As a result, values of the impedance would ideally be R/2, R/3, and R/4 in these cases, respectively. When reciprocals (1/S) of the areas are plotted on the horizontal axis, and values of the impedance are plotted on the vertical axis, a slope (ΔR) can be obtained based on linear approximation. The resistivity of the powdery catalyst can be calculated based on the following formula (4).

$$\text{Resistivity } (\Omega \cdot cm) = \Delta R / L \quad (4)$$

In FIGS. 1 to 4C, to simplify descriptions on the measurement method, a case in which eight first electrodes $1a$ to $1h$ and eight measurement chambers $3a$ to $3h$ are provided is described. However, the presence of two or more first electrodes, and two or more measurement chambers may be sufficient for practical measurements.

The number of the measurement chambers 3 is preferably three or more, and one hundred or less. In cases where the number of the measurement chambers 3 is less than three, only a few points are available for the linear approximation to calculate the above-mentioned value ΔR. As a result, accurate values may not be obtained. On the other hand, in cases where the number of the measurement chambers 3 is more than one hundred, it may take a long time for the measurement, and therefore, the presence of such a number of the measurement chambers may not be practical.

According to this embodiment, while multiple first electrodes are used to vary the electrode area, the measurement is carried out. Accordingly, the measurement accuracy can be improved. Additionally, by supplying a gas to the measurement chambers 3, evaluations consistent with actual use environments become possible.

The above-described operations are controlled by the control unit 18.

EXAMPLE 1

[Production of the First Electrode Unit 6]

The first electrodes $1a$ to $1h$ were produced with an iron, and were subjected to gold plating. Each of the first electrodes $1a$ to $1h$ was formed in a cylindrical shape with a diameter of 3 mm, and the eight first electrodes $1a$ to $1h$ were immobilized in a first insulator 2 made of a polyphenylene sulfide resin, along a concentric circle having a diameter of 30 mm.

[Production of the Second Electrode Unit 7]

The second electrode 5 was produced with a sintered metal material (model number "ESS-40-40-1-2" manufactured by SMC CORPORATION), and was subjected to gold plating. Eight through-holes each having a diameter of 3 mm were formed in a second insulator 4 made of a polyphenylene sulfide resin, in a concentric pattern. The second electrode 5 and the second insulator 4 were immobilized to one another, and the above through-holes were employed as measurement chambers $3a$ to $3h$.

[Loading of Measurement Samples]

A carbon black material (model number "ECP" manufactured by LION CORPORATION) was provided as measurement samples. 0.2 mg of the material was put into each of the measurement chambers 3. A leveling mount (model number "KHWM-SC56" manufactured by MISUMI GROUP INC.) was used as a pressing unit, and a pressure-sensitive element (model number "LUR-A-2KNSA1" manufactured by KYOWA ELECTRONIC INSTRUMENTS CO., LTD.) was used as a pressure-measuring unit, thereby carrying out loading adjustments based on application of pressure.

[Method for Varying Measurement Environments]

The air was supplied to the gas-flow channel 11 to thereby convert the insides of the measurement chambers $3a$ to $3h$ to air-present environments, and then, the measurements were conducted.

[Method for Measuring a Distance Between the Electrodes]

A thickness-measuring device 15 (model number "GT2-H12K" manufactured by KEYENCE CORPORATION) was provided. In advance, measurements were conducted in conditions in which any test samples $9a$ to $9h$ were not provided. Then, measurements were conducted in conditions in which the test samples $9a$ to $9h$ were provided in the resistance-measurement apparatus. A difference between these measured values was considered as a thickness L of each of the test samples $9a$ to $9h$. The results are shown in Table 1.

TABLE 1

| | | Pressing force (Mpa) | | | | | | | | |
|---|---|---|---|---|---|---|---|---|---|---|
| | | 4 | 6 | 8 | 10 | 12 | 14 | 16 | 18 | 20 |
| EXAMPLE 1 Carpon (in the air) | Thickness L (um) | 450.5 | 385.5 | 351.9 | 325.1 | 304.7 | 287.5 | 278.7 | 267.2 | 262.9 |
| | ΔR (Ω · cm^2) | 0.0073 | 0.0050 | 0.0036 | 0.4336 | 0.0022 | 0.0022 | 0.0020 | 0.0017 | 0.0016 |
| | Resistivity (Ω · cm) | 0.1615 | 0.1286 | 0.1035 | 0.0971 | 0.0737 | 0.0780 | 0.0701 | 0.0653 | 0.0598 |

[Method for Measuring Impedance Values]

An AC impedance meter (model number "3532-80" manufactured by HIOKI E.E. CORPORATION) was provided. AC waves with a frequency of 1 kHz to 1 MHz and an amplitude of 10 mV were applied to the test samples. With regard to frequencies of the AC waves, frequencies that exhibited a phase of 0 in the AC impedance measurement were selected. Based on the signal selector, values of impedance were measured in cases where one, two, four, seven, and eight first electrodes were elected.

[Method for Computing Resistivities]

Data of the measured impedance values were plotted on a vertical axis, and data of reciprocals of the electrode areas were plotted on a horizontal axis, to thereby generate a graph. A slope (ΔR) of a line based on linear approximation was obtained for the resulting graph. Resistivities of the test samples $9a$ to $9h$ were calculated based on above formula (4). Results obtained through the measurements by varying pressing conditions are shown in Table 1.

Figure 6:
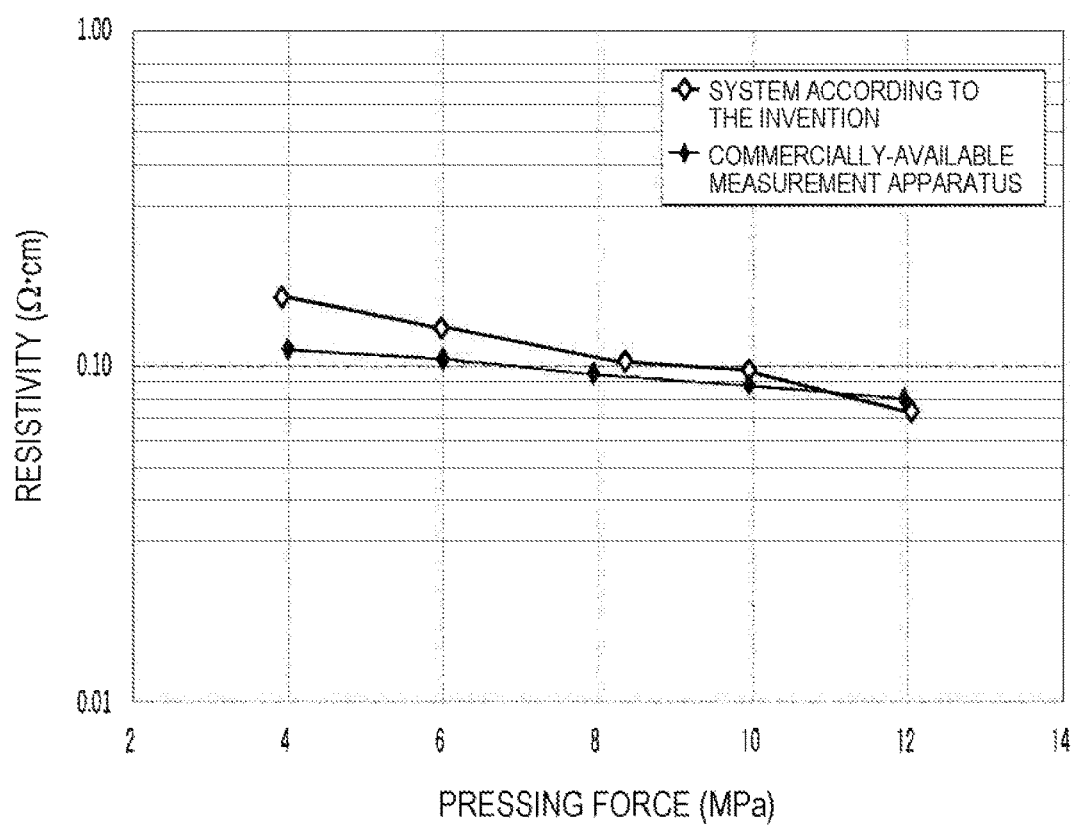
FIG. 6 is a diagram that shows results of measurements in EXAMPLE 1.

FIG. 6 is a graph showing the results in Table 1. Pressing forces during the measurement are plotted on the horizontal axis, while resistivities are plotted on the vertical axis.

As a standard for comparison, a carbon black material (model number "ECP" manufactured by LION CORPORATION) was subjected to measurements based on a commercially-available measurement apparatus (model number "MCP-PD51" manufactured by MITSUBISHI CHEMICAL ANALYTECH CO., LTD.). In this commercially-available apparatus, only one first electrode 1 and one second electrode 5 are provided. It took a long time to conduct the measurements by use of large amounts of specimens. A graph of the results is shown in FIG. 6. Pressing forces during the measurement are plotted on the horizontal axis, while resistivities are plotted on the vertical axis. Measurement values obtained in EXAMPLE 1 are almost consistent with the measurement values obtained by use of the commercially-available apparatus.

Thus, it was confirmed that resistivities of the powdery materials can be highly accurately measured based on the present measurement method.

EXAMPLE 2

Differences between EXAMPLE 2 and EXAMPLE 1 will be described. Unless otherwise specified, the same conditions as those in EXAMPLE 1 were adopted.
[Loading of Measurement Samples]

Platinum-supported carbon materials (model number "TEC10EA50E" manufactured by TANAKA KIKINZOKU KOGYO K.K.) were provided as measurement samples. 2.5 mg of the material was loaded into each of the measurement chambers 3a to 3h.
[Method for Varying Measurement Environments]

The air was supplied to the gas-flow channel to thereby convert the insides of the measurement chambers 3a to 3h to air-present environments, and then, measurements were conducted. Then, a hydrogen gas was supplied to the gas-flow channel to convert the insides of the measurement chambers 3 to hydrogen environments, and measurements were conducted. Results obtained through the measurements conducted by varying pressing conditions are shown in Table 2.

Thus, it was confirmed that variations in the resistivities depending on environments for measurements of powdery catalysts can be measured based on the present measurement method.

According to EXAMPLE 1, influences of errors on measurement values such as values relating to contact resistance between the powdery catalysts and the electrodes can be reduced by measuring resistivities of the powdery catalysts at multiple points having different areas. As a result, resistivities of powdery catalysts can accurately be measured based on the present measurement method. Furthermore, according to EXAMPLE 2, powdery catalysts can be evaluated under conditions closer to environments where they are practically used, by way of varying surrounding environments during the measurements.

In addition, only based on the measurement unit 8 and the measuring device 13, properties of powdery materials can be measured even by using slight amounts of the powdery materials. The signal selector 12, the thickness-measuring device 15, the gas-flow channel 11, the pressing unit 16, etc. are preferably provided.

The resistance-measurement apparatus and method according to the disclosure can be employed for evaluations on catalysts that would be used for not only fuel cells but also any other various devices. Furthermore, the resistance-measurement apparatus and method can be employed for evaluations on powdery materials other than such catalyst materials.

What is claimed is:
1. A resistance-measurement apparatus, comprising:
multiple measurement chambers for holding powdery materials;
multiple first electrodes that press the respective powder materials in the measurement chambers;

TABLE 2

| | | | Pressing force (Mpa) | | | | | | |
|---|---|---|---|---|---|---|---|---|---|
| | | | 1 | 2 | 3 | 4 | 6 | 8 | 10 |
| EXAMPLE 2 Platinum-supported carbon | In the air | Thickness L (um) | 424.9 | 370.2 | 329.2 | 303.3 | 253.5 | 246.8 | 225.6 |
| | | ΔR (Ω · cm^2) | 0.0308 | 0.0205 | 0.0143 | 0.0116 | 0.0072 | 0.0065 | 0.0051 |
| | | Resistivity (Ω · cm) | 0.7253 | 0.5524 | 0.4340 | 0.3811 | 0.2823 | 0.2641 | 0.2254 |
| | In the hydrogen gas | Thickness L (um) | 343.3 | 301.8 | 257.3 | 215.1 | 186.1 | 170.8 | 168.7 |
| | | ΔR (Ω · cm^2) | 0.0117 | 0.0081 | 0.0059 | 0.0042 | 0.0032 | 0.0025 | 0.0023 |
| | | Resistivity (Ω · cm) | 0.3407 | 0.2674 | 0.2300 | 0.1949 | 0.1694 | 0.1469 | 0.1352 |

Figure 7:
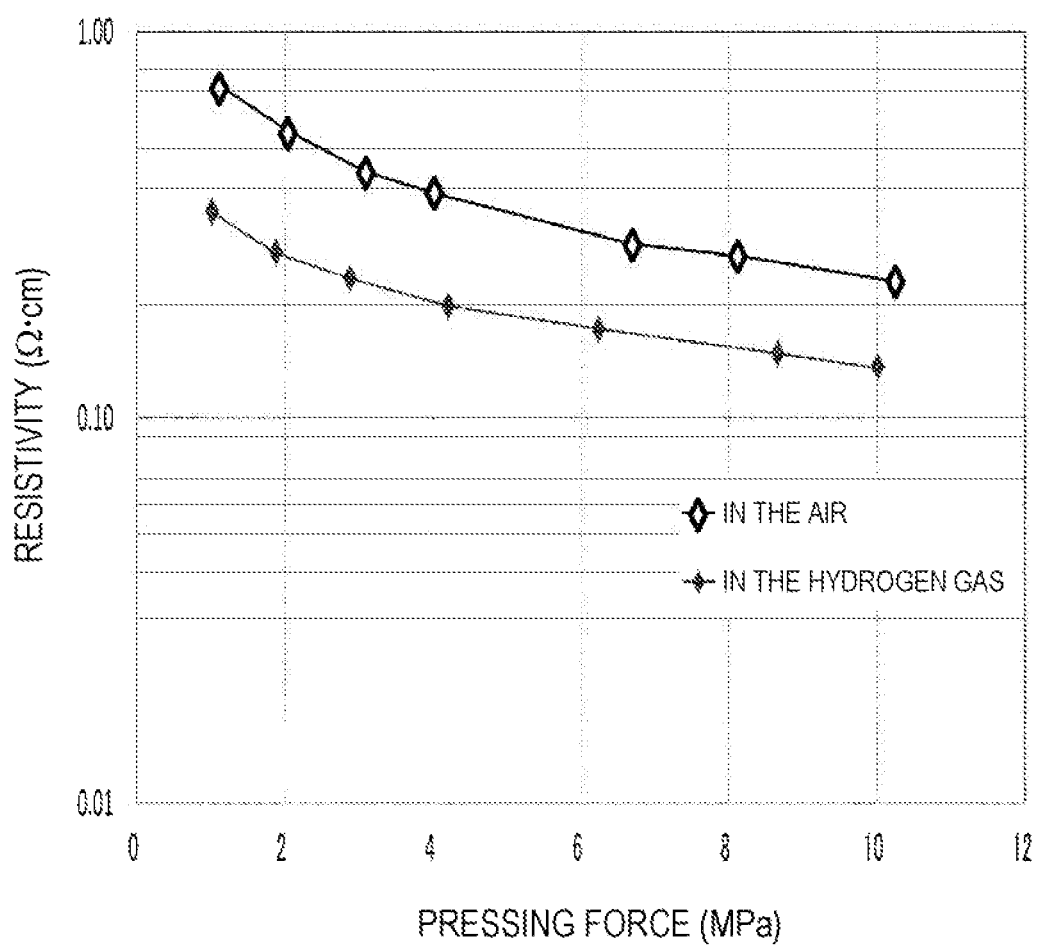
FIG. 7 is a diagram that shows results of measurements in EXAMPLE 2.
Figure 8:
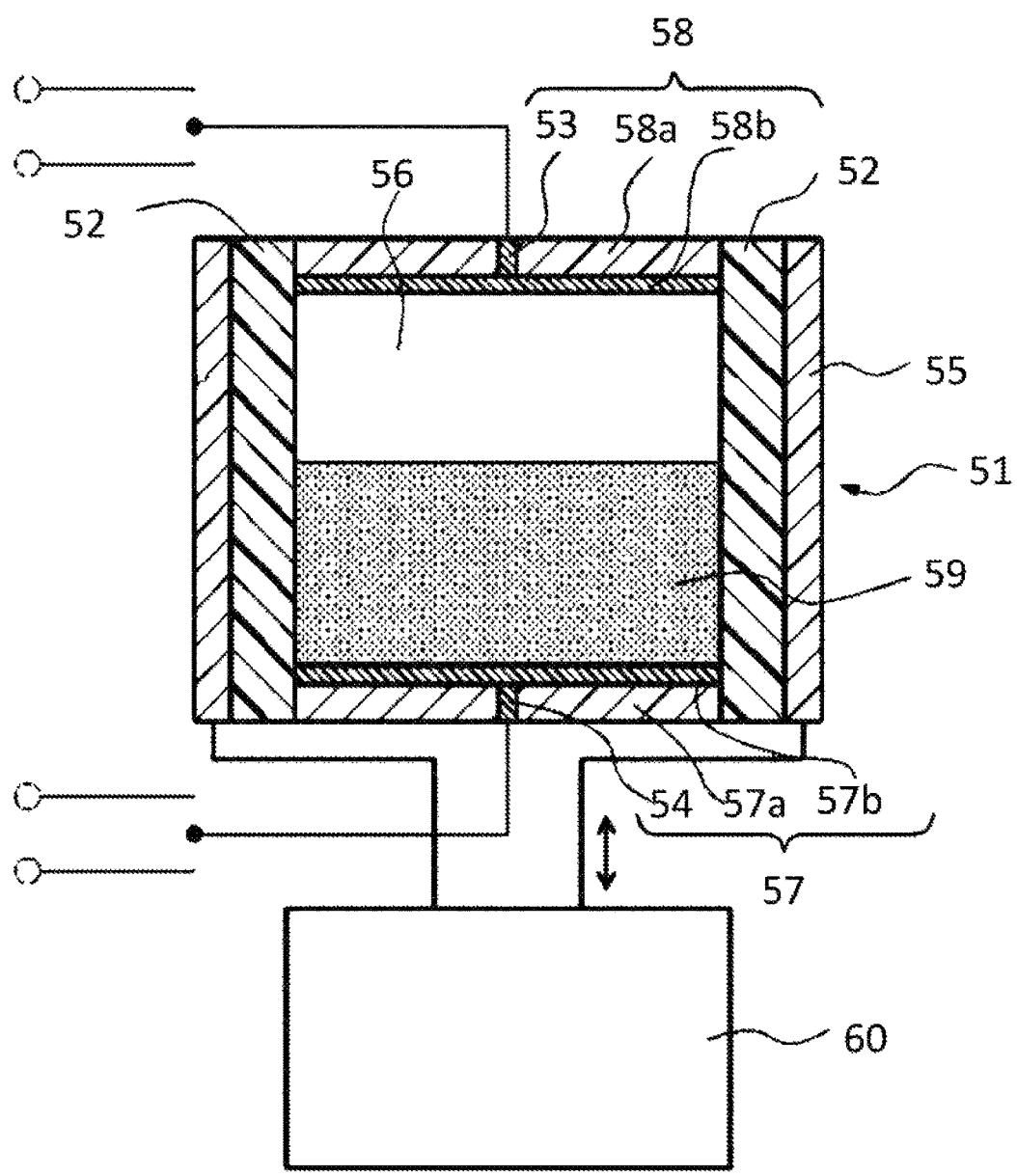
FIG. 8 is a schematic view of the conventional method for measurement of resistance of powdery materials.

The results shown in Table 2 is shown as a graph in FIG. 7. Pressing forces during the measurements are plotted on the horizontal axis, while resistivities are plotted on the vertical axis.

As compared with the case in which the measurements were conducted in the air, the resistivities became lower in the case in which the measurements were conducted in the hydrogen gas. The reason for this phenomenon is considered as follows. That is, hydrogen molecules were dissociated into hydrogen ions and electrons due to the presence of platinum-supported carbon materials, which were measurement samples, the measured current values were increased due to influences of an increase in the number of electrons, and the resistivities became lower.

at least one second electrode that faces the first electrodes and that presses the powdery materials; and
a measuring device that measures a resistance between the first electrodes and the at least one second electrode,
wherein the at least one second electrode comprises only one second electrode.
2. The resistance-measurement apparatus according to claim 1, further comprising a first insulator that holds the first electrodes.
3. The resistance-measurement apparatus according to claim 1, further comprising a second insulator, wherein the measurement chambers are provided in said second insulator.

4. The resistance-measurement apparatus according to claim 1, wherein the first electrodes and the measurement chambers are arranged so as to be paired with each other.

5. The resistance-measurement apparatus according to claim 1, further comprising a control unit that computes the resistance based on a value of impedance between the first electrodes and the at least one second electrode.

6. The resistance-measurement apparatus according to claim 1, wherein at least one member selected from the group consisting of the first electrodes, the at least one second electrode, and the measurement chambers has gas permeability.

7. The resistance-measurement apparatus according to claim 1, further comprising a gas flow channel, wherein at least one member selected from the group consisting of the first electrodes, the at least one second electrode, and the measurement chambers is connected to said gas flow channel.

8. The resistance-measurement apparatus according to claim 1, wherein the first electrodes comprise three or more first electrodes, and the measurement chambers comprise three or more measurement chambers.

9. The resistance-measurement apparatus according to claim 1, further comprising a pressing mechanism that presses a space between the first electrodes and the at least one second electrode.

10. The resistance-measurement apparatus according to claim 1, further comprising a measurement unit that measures a distance between the first electrodes and the at least one second electrode.

11. The resistance-measurement apparatus according to claim 1, further comprising a signal selector that selects an electrical connection between the first electrodes and the measuring device.

12. A resistance-measurement method, comprising:
(i) placing at least one powdery material between a number N of first electrodes and at least one second electrode, and pressing the at least one powdery material therebetween;
(ii) measuring an impedance between the number N of the first electrodes and the at least one second electrode; and
(iii) measuring an impedance between a number M of the first electrodes and the at least one second electrode, wherein the number N is different from the number M,
wherein the at least one second electrode comprises only one second electrode.

13. A resistance-measurement apparatus, comprising:
multiple measurement chambers for holding powdery materials;
multiple first electrodes that press the respective powder materials in the measurement chambers;
at least one second electrode that faces the first electrodes and that presses the powdery materials; and
a measuring device that measures a resistance between the first electrodes and the at least one second electrode,
wherein the multiple first electrodes are arranged in a concentric circle pattern.

14. A resistance-measurement apparatus, comprising:
multiple measurement chambers for holding powdery materials;
multiple first electrodes that press the respective powder materials in the measurement chambers;
at least one second electrode that faces the first electrodes and that presses the powdery materials; and
a measuring device that measures a resistance between the first electrodes and the at least one second electrode,
wherein the multiple first electrodes are arranged in a symmetric pattern.

* * * * *